(12) United States Patent
Wang et al.

(10) Patent No.: US 10,457,645 B2
(45) Date of Patent: Oct. 29, 2019

(54) METHOD FOR THE PREPARATION OF 3-FLUOROALKYL-1-METHYLPYRAZOL-4-CARBOXYLIC ACID

(71) Applicants: SOLVAY FLUOR GmbH, Hannover (DE); Changzhou Keylab Biochemical Co., Ltd., Changzhou, Jiangsu (CN)

(72) Inventors: Mingchun Wang, Jiangsu (CN); Qingyi Li, Jiangsu (CN)

(73) Assignee: CHANGZHOU KEYLAB BIOCHEMICAL CO., LTD., Changzhou (CN)

( * ) Notice: Subject to any disclaimer, the term of this patent is extended or adjusted under 35 U.S.C. 154(b) by 0 days.

(21) Appl. No.: 15/763,472

(22) PCT Filed: Sep. 28, 2016

(86) PCT No.: PCT/IB2016/001462
§ 371 (c)(1),
(2) Date: Mar. 27, 2018

(87) PCT Pub. No.: WO2017/064550
PCT Pub. Date: Apr. 20, 2017

(65) Prior Publication Data
US 2018/0273486 A1 Sep. 27, 2018

(30) Foreign Application Priority Data
Sep. 28, 2015 (WO) ............... PCT/CN2015/090970

(51) Int. Cl.
*C07D 231/14* (2006.01)
*A01N 43/56* (2006.01)

(52) U.S. Cl.
CPC ........... *C07D 231/14* (2013.01); *A01N 43/56* (2013.01)

(58) Field of Classification Search
CPC .................................................. C07D 231/14
See application file for complete search history.

(56) References Cited

FOREIGN PATENT DOCUMENTS

| WO | 2009133178 A1 | 5/2008 |
| WO | 2009000442 A2 | 12/2008 |
| WO | 2009043444 A1 | 4/2009 |
| WO | 2009106619 A1 | 9/2009 |
| WO | 2011113788 A1 | 3/2010 |
| WO | 2012025469 A1 | 3/2012 |
| WO | 2016152886 A1 | 3/2015 |

OTHER PUBLICATIONS

Etsuji Okada et al: "Facile Synthetic Methods for 3- and 5-Trifluoromethyl-4-Trifluoroacetyl-Pyrazoles and Their Conversion into Pyrazole-4-Carboxylic Acids", Heterocycles Communication | Special Issue, Japan Institute of Heterocyclic Chemistry, JP, vol. 34, No. 4, Jan. 1, 1992 (Jan. 1, 1992), pp. 791-798.
Kramer, Wolfgang et al: "Chapter 15: Fungicides Acting on Oxidative Phosphorylation", Modern Crop Protection Compounds, vol. 1-3, Second Edition, pp. 627-639, Wiley 2012.

*Primary Examiner* — Shawquia Jackson
(74) *Attorney, Agent, or Firm* — Gokalp Bayramoglu

(57) ABSTRACT

The present invention relates to method for the preparation of 3-fluoroalkyl-1-methylpyrazol-4-carboxylic acid, wherein it comprises the following steps: step 1, fluoroacetyl fluoride derivative shown in Formula I undergoes condensation with dimethylamino vinyl methyl ketone, as a result, 3-dimethylamino methylene-fluoro-2,4-pentanedione derivative shown in Formula II is formed; step 2, ring closing reaction takes place between said 3-dimethylamino methylene-fluoro-2,4-pentanedione shown in Formula II and methylhydrazine, in this way, 3-fluoroalkyl-1-methyl-4-acetyl pyrazol derivative shown in Formula III is obtained; step 3, the said 3-fluoroalkyl-1-methyl-4-acetyl pyrazol derivative shown in Formula III is oxidized in the presence of alkali, and then acidified, in this way, 3-fluoroalkyl-1-methylpyrazol-4-carboxylic acid shown in Formula IV is formed. Preparing method of present invention, wherein the required preparing route is simple, the raw material cost is low, the resulting yield of each step is high, and it is suitable for industrialization.

13 Claims, 3 Drawing Sheets

METHOD FOR THE PREPARATION OF 3-FLUOROALKYL-1-METHYLPYRAZOL-4-CARBOXYLIC ACID

This application is a U.S. national phase entry under 35 U.S.C. § 371 of International Application No. PCT/IB2016/001463, filed on Sep. 28, 2016, which claims priority to International Application No. PCT/CN2015/090970, filed on Sep. 28, 2015. The entire contents of these applications are explicitly incorporated herein by this reference.

FIELD OF THE INVENTION

The present invention relates to a method for the industrial preparation of 3-fluoroalkyl-1-methylpyrazol-4-carboxylic acid.

BACKGROUND OF THE INVENTION

At present, the total volume of global fluorine products (including inorganic fluorine) is 2.5 million ton, and the total sales is above 21 billion USD. In recent five years, the annual growth rate of fluorine products is around 3.5% globally. There are more than 100 different types of inorganic fluorine products, the total volume is around one million tons, and the total sales is about two billion US dollars, furthermore, more than half of said inorganic fluorine products is used in electronic chemicals, optical materials and catalysts; there are more than 1000 types of fluorine-containing fine chemicals, the total sales is around fifty billion US dollars, which is 70% of the total sales of the fluorine products. In particular, the development of fluorine-containing pesticides is very rapid, several key fluorine/nitrogen-containing heterocyclic sterilization products have been developed based on studies on activities, structures and functional mechanisms.

Among fluorine-nitrogen heteocyclic compounds, 3-fluoroalkyl-1-methylpyrazol-4-carboxylic acid is an important intermediate. For instance, 3-(difluoromethyl)-1-methyl-1H-pyrazol-4-carboxylic acid (CAS: 176969-34-9) is an important intermediate for pesticides. It plays significantly important roles in many newly developed pesticides, for instance, grain fungicide Bixafen developed by Bayer Cropscience AG, new fungicide Fluxapyroxad developed by BASF, Isopyrazam and Sedaxane developed by Syngenta, etc.

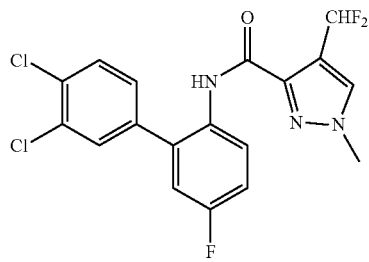

Bixafen
Bayer Cropscience

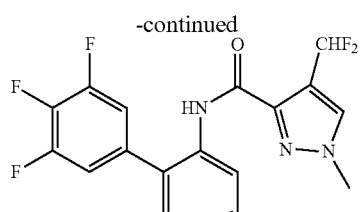

Fluxapyroxad
BASF

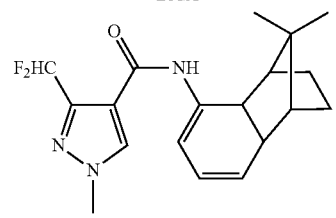

Isopyrazam
Syngenta

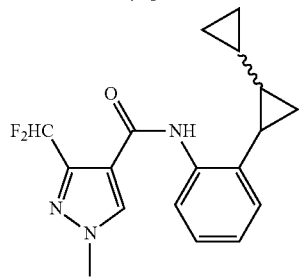

Sedaxane
Syngenta

Due to the fact that 3-(difluoro)-1-methyl-1H-pyrazol-4-carboxylic acid is a key intermediate used for preparation of said novel amide fungicides, extensive attention is drawn to its synthetic process, and current preparing methods are summarized below:

1. Claisen condensation of difluoroethyl acetate. At present, it is widely used in industrial mass production, and the preparing method was disclosed in patent publication no. WO2009106619 by BASF. The processing procedure is: difluoroethyl acetoacetate is obtained via Claisen condensation of difluoroethyl acetate, subsequently, the obtained undergoes condensation with triethyl orthoformate and forms 4,4-difluoro-2-(ethoxymethylene)-3-oxoethyl butyrate, subsequently, ring closure takes place between said compound and methylhydrazine, in this way, 3-(difluoromethyl)-1-methyl-1H-pyrazol-4-carboxylic ethyl ester (DFMMP) is formed, which then undergoes hydrolysis with NaOH and acidified with HCl, in this way, 3-(difluoromethyl)-1-methyl-1H-pyrazol-4-carboxylic acid (DF-PA) is formed. Wherein, the preparation of difluoroethyl acetate has been reported in a number of inventions, it could be prepared from tetrafluoroethylene monomer, wherein tetrafluoroethyl ether intermediate is formed, and then difluoroethyl acetate is obtained via a two-step reaction. It could also be prepared from dichloroethyl acetate, wherein chlorine atom is converted to fluorine atom with the aid of KF. The said preparing route is classic, with relatively high yield, and the resulting production is stable, however, the disadvantages include relatively long synthetic route, and relatively large amount of waste gas, waste water and waste solid being generated.

2. Dimethyl amino ethyl acrylate method. The said method was disclosed in patent publication no. WO2009043444 by Bayer, furthermore, a similar method, in which dimethyl amino group is replaced by cyclohexyl amino group, was disclosed in patent publication no. WO2009133178 by BASF. The processing procedure of said method is as follows: difluoro acetylfluoride gas is introduced to dimethyl amino ethyl acrylate, the obtained intermediate directly reacts with methylhydrazine, the said ring closure results in formation of 3-(difluoromethyl)-1-methyl-1H-pyrazol-4-carboxylic ethyl ester (DFMMP), the said compound undergoes hydrolysis with the presence of NaOH, and then is acidified with the aid of HCl, in this way, 3-(difluoromethyl)-1-methyl-1H-pyrazol-4-carboxylic acid (DFPA) is formed. Wherein, difluoro acetylfluoride gas is obtained via high temperature splitting of tetra-fluoro diethyl ether. The design of said route is rather delicate, only a few steps are required and the resulting yield is high. However, the synthetic cost of dimethyl amino ethyl acrylate is relatively high.

3. Difluorochloroacetyl chloride method. The said method was disclosed in patent publication no. WO2012025469 by Solvay. The said processing procedure is as follows: difluorochloroacetyl chloride (CDFAC) is used as a starting material, and reacts with ethenone, and quenched with the aid of ethanol, in this way, difluorochloroacetyl ethyl acetate is formed, subsequently, 3-(difluorochloromethyl)-1-methyl-1H-pyrazol-4-ethyl carboxylate is formed using method similar to said Claisen condensation, the obtained is reduced with the aid of zinc powder or hydrocarbonized with the aid of Pd, leading to formation of 3-(difluoromethyl)-1-methyl-1H-pyrazol-4-carboxylic ethyl ester (DFMMP), the obtained is hydrolyzed with the aid of NaOH and acidified with the presence of HCl, in this way, 3-(difluoromethyl)-1-methyl-1H-pyrazol-4-carboxylic acid (DFPA) is formed. The resulting yield of said method is high, the obtained atom economy is attractive, the required cost is relatively low, and only a small amount of waste gas, waste water and waste solid is generated. However, the disadvantages include: the required processing is rather long, difluorochloroacetyl chloride has to be obtained via photooxidation, the equipment investment is high, and furthermore, one additional step of reduction and chlorine removal is required.

4. Other synthetic methods. 1) patent publication no. EP2008996 disclosed a method, wherein dichloroacetyl chloride, vinyl ether and methylhydrazine react and form 3-(difluoromethyl)-1-methyl-1H-pyrazol-4-carboxylic acid via five-step reaction. Although, the production cost is further controlled, the required reaction conditions are rather harsh, wherein dichloroacetyl chloride and vinyl ether have to be reacted at −40~−20° C.; the reaction temperature for introducing carboxylic group via catalytic pressurization is 150° C., the pressure of reaction kettle has to be adjusted from time to time, and therefore, it is not easy to operate, furthermore, the obtained isomers are difficult to separate. 2) patent publication no. WO2009000442 disclosed a method, wherein difluoro ethyl acetate is used as starting material, it reacts with hydrazine hydrate and forms hydrazide, subsequently, the obtained undergoes methylation and ring closure with the aid of ethyl propiolate, leading to formation of 3-(difluoromethyl)-1-methyl-1H-pyrazol-4-carboxylic ethyl ester (DFMMP), however, the resulting yield of said method is relatively low, the price of said ethyl propiolate is rather high, and therefore, it is not suitable for industrialization.

SUMMARY OF THE INVENTION

The present invention provides a method for preparation of 3-difluoromethyl-1-methylpyrazol-4-carboxylic acid which is suitable for industrialization, wherein the reaction route is relatively short, the required raw material cost is relatively low, and the yield of each step is relatively high, furthermore, the present invention also provides 3-fluoroalkyl-1-methylpyrazol-4-carboxylic acid obtained by the said method.

In order to solve the above technical problems, one embodiment of the present invention provides a method for the preparation of 3-fluoroalkyl-1-methylpyrazol-4-carboxylic acid, wherein it comprises the following steps:

Step 1, fluoroacetyl fluoride derivative shown in Formula I undergoes condensation with dimethyl amino vinyl methyl ketone, as a result, 3-dimethylamino methylene-1,1-difluoro-2,4-pentanedione derivative shown in Formula II is formed,

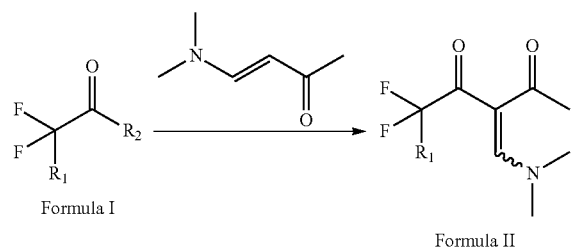

Formula I

Formula II wherein, $R_1$ is hydrogen, fluorine or chlorine atom; $R_2$ is fluorine or chlorine atom.

Step 2, ring closing reaction takes place between said 3-dimethylamino methylene-1,1-difluoro-2,4-pentanedione shown in Formula II and methylhydrazine, in this way, 3-fluoroalkyl-1-methyl-4-acetyl pyrazol derivative shown in Formula III is obtained.

Formula II

Formula III

Step 3, the said 3-fluoroalkyl-1-methyl-4-acetyl pyrazol derivative shown in Formula III is oxidized in the presence of alkali, and then acidified, in this way, 3-fluoroalkyl-1-methylpyrazol-4-carboxylic acid shown in Formula IV is formed.

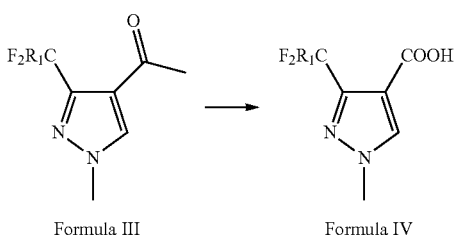

Formula III → Formula IV

Preferably, in step 1, a gas of the fluoroacetyl halide derivative of said Formula I is directly introduced to a dichloromethane solution containing dimethyl amino vinyl methyl ketone, and the reaction temperature is −5~0° C.

Preferably, in step 2, the reaction temperature is −40~0° C., the reaction time is 1~8 h, and the molar ratio between said methylhydrazine and 3-dimethylamino methylene-1,1-difluoro-2,4-pentanedione derivative is 1.1:1~1.5:1.

More preferably, the reaction temperature of said step 2 is −25~−20° C., and the reaction time is 1~2 h.

Preferably, in step 2, the ring closing reaction between said 3-dimethylamino methylene-1,1-difluoro-2,4-pentanedione shown in Formula II and methylhydrazine takes place in the presence of dimethylamine. In particular, the dimethylamine is provided in the form of an aqueous solution. The molar ratio of dimethylamine to said 3-dimethylamino methylene-1,1-difluoro-2,4-pentanedione shown in Formula II may be in the range of 1.5:1~2.5:1. Without wishing to be bound by theory, it is believed that the addition of dimethylamine can enhance the yield of the reaction.

Preferably, in step 3, oxidation takes place in sodium hypochlorite or sodium hypobromite solution in the presence of alkali, the said sodium hypochlorite solution is obtained by introducing chlorine gas to NaOH water solution, and the said sodium hypobromite solution is obtained by introducing liquid bromine to NaOH water solution.

Preferably, in step 3, the reaction temperature is 0~50° C., and the reaction time is 1~5 h.

More preferably, in step 3, the reaction temperature is 10~20° C., and the reaction time is 2~3 h.

Preferably, in step 3, HCl solution is used in acidification, and the final pH value is adjusted to 1~2.

Preferably, said fluoroacetyl halides of Formula I is difluoroacetyl fluorine, and said 3-fluoroalkyl-1-methylpyrazol-4-carboxylic acid of Formula IV is 3-(difluoromethyl)-1-methyl-1H-pyrazol-4-carboxylic acid. The present invention further provides 3-fluoroalkyl-1-methylpyrazol-4-carboxylic acid obtained by the method described herein.

The advantages of the present invention include: the reaction route of the method for the preparation of 3-fluoroalkyl-1-methylpyrazol-4-carboxylic acid is relatively short, the cost of required raw materials is low, the method is safe and reliable, the resulting yield of each step is relatively high, the obtained atom economy is attractive and the product quality is high. Method of the present invention is easy to operate, a small amount of waste gas, waste water and waste solid is generated, it is suitable for industrialization, furthermore, the method for the preparation of dimethylamino vinyl methyl ketone in the present invention is simple.

ILLUSTRATION OF THE FIGURES

EXAMPLES

Example 1

Figure 1:
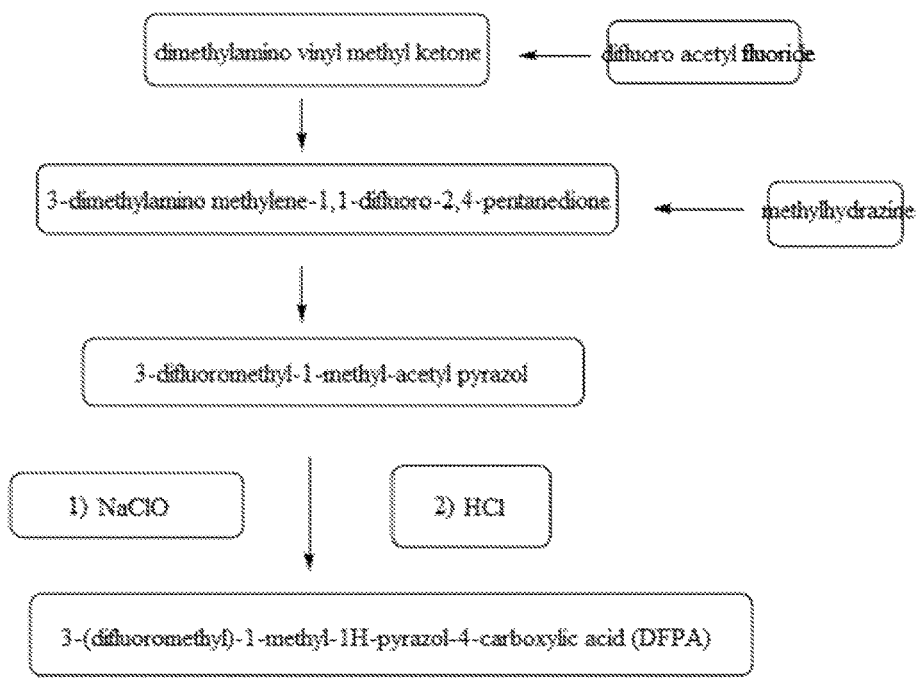
FIG. 1 is reaction flow chart of preparation of 3-(difluoromethyl)-1-methyl-1H-pyrazol-4-carboxylic acid in Example 1 of the present invention.

As shown in FIG. 1, method for the preparation of 3-(difluoromethyl)-1-methyl-1H-pyrazol-4-carboxylic acid of present Example comprises the following steps:

Preparation of 3-dimethylamino methylene-1,1-difluoro-2,4-pentanedione 565 mL dichloro methane solution containing dimetylamino vinyl methyl ketone is added to a three-neck flask, the said solution contains 113 g (1.0 mol) dimethylamino vinyl methyl ketone. The said solution is cooled to −5° C. in the presence of nitrogen. Subsequently, 108 g (1.1 mol) difluoroacetyl fluorine gas is introduced. The temperature of said system is controlled to below 0° C. during addition of said gas, at the end of addition; the said mixture is mixed for 2 h at said temperature. The obtained reaction solution is vacuum condensed to remove the said solvent with the aid of rotary evaporator, the obtained is crude 3-dimethylaminomethylene-1,1-difluoro-2,4-pentanedione, the resulting gas-phase purity is above 95%, and the said crude product is directly used in the following reaction based on quantitative yield.

The said difluoroacetyl fluorine gas is obtained via high temperature splitting of tetrafluorodiethyl ether, the required reaction temperature is 300° C., and aluminium phosphate inorganic salt is used as the catalyst.

The said dimethylamino vinyl methyl ketone is prepared via condensation of acetone, ethyl formate and sodium methoxide, subsequently, the obtained is treated with dimethylamino hydrochloride. The reaction is as follows:

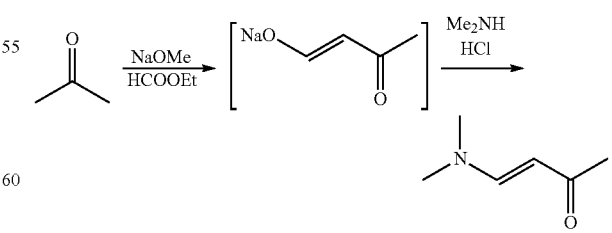

Method for the preparation of dimethylamino vinyl methyl ketone is rather simple; the required cost is relatively low, leading to attractive cost control of the method of the present invention.

Preparation of 3-difluoromethyl-1-methyl-4-acetyl pyrazol

40% methylydrazine water solution is added to a three-neck flask, wherein the said solution contains 126 g (1.1 mol). The said solution is cooled to −20° C., subsequently, the said dichloromethane solution containing 3-dimethylamino methylene-1,1-difluoro-2,4-pentanedione is added to said flask, the said addition takes place at −25~−20° C., at the end of said addition, the said mixture is kept at said temperature for 1 h. Once GC shows raw materials are completely reacted, the said mixture is heated to room temperature, subsequently, water phase is separated, the obtained organic phase is condensed, and then it is recrystallized and dried, in this way, 148 g white solid is obtained, and the resulting yield is 85%.

Figure 2:
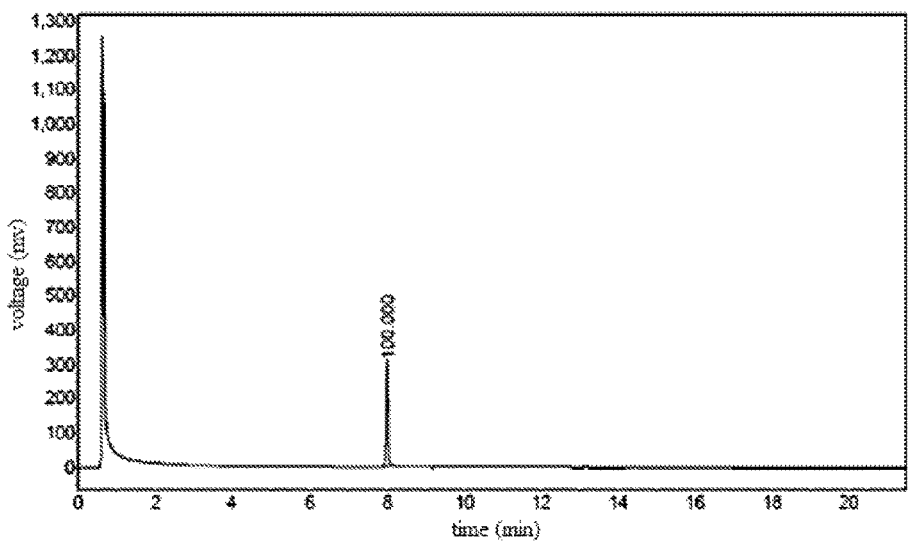
FIG. 2 is GC spectrum of 3-difluoromethyl-1-methyl-4-acetyl pyrazol synthesized in Example 1 of the present invention.

As shown in FIG. 2, the purity of said white solid is analyzed with the aid of GC, and the obtained results are listed in Table 1.

TABLE 1

GC results of 3-difluoromethyl-1-methyl-4-acetyl pyrazol

| Peak no. | Retention time (min) | Peak height | Peak area | Content (%) |
|---|---|---|---|---|
| 1 | 7.998 | 302654.188 | 1048392.313 | 100.0000 |
| Total | 7.998 | 302654.188 | 1048392.313 | 100.0000 |

Figure 3:
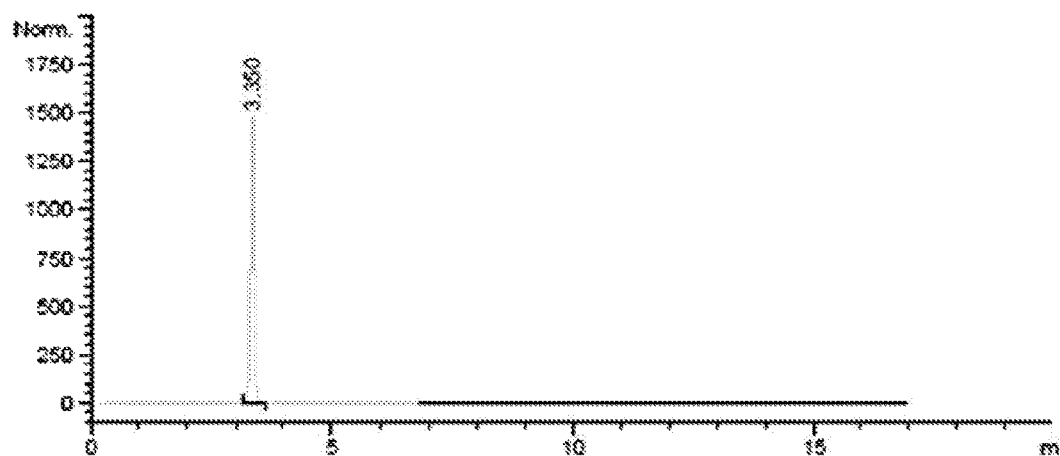
FIG. 3 is HPLC spectrum of 3-difluoromethyl-1-methyl-4-acetyl pyrazol synthesized in Example 1 of the present invention.

As shown in FIG. 3, the purity of said white solid is analyzed with the aid of HPLC, and the obtained results are listed in Table 2.

TABLE 2

HPLC results of 3-difluoromethyl-1-methyl-acetyl pyrazol

| Peak no. | Retention time (min) | Peak height | Peak area | Content (%) |
|---|---|---|---|---|
| 1 | 3.350 | 1483.95544 | 8274.68066 | 100.0000 |
| Total | 3.350 | 1483.95544 | 8274.68066 | 100.0000 |

Figure 4:
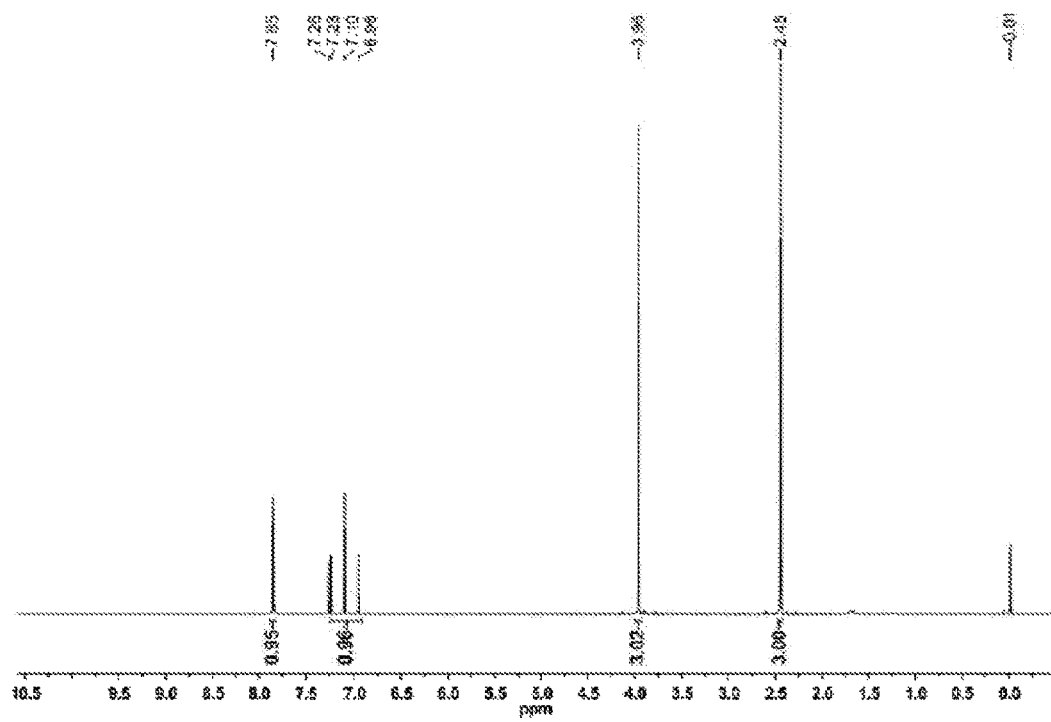
FIG. 4 is NMR spectrum of 3-difluoromethyl-1-methyl-4-acetyl pyrazol synthesized in Example 1 of the present invention.

As shown in FIG. 4, the resulting purity of said white solid is double verified with the aid of GC and HPLC, subsequently, $^1$HNMR is conducted on said white solid with the aid of Bruker 400M NMR spectrometer, wherein CDCl$_3$ is served as solvent, and the obtained NMR results are as follows:

HNMR (CDCl$_3$, 400M): δ=7.85 (s, 1H), 7.24 (d, J=12 Hz, 1H), 7.10 (s, 1H), 6.96 (s, 1H), 3.96 (s, 3H), 2.45 (s, 3H).

The structure of said white solid is determined to be 3-difluoromethyl-1-methyl-4-acetyl pyrazol, wherein it is used in the following reaction.

Preparation of 3-(difluoromethyl)-1-methyl-1H-pyrazol-4-carboxylic acid 887.5 g 10% NaCLO water solution is added to a three-neck flask. The said reaction solution is cooled to 10° C. Subsequently, 100 g 3-difluoromethyl-1-methyl-4-acetyl pyrazol is dissolved in 100 mL methanol, leading to formation of organic solution. The said organic solution is slowly added to the said flask. The temperature of said addition is kept at 10~15° C. At the end of said addition, the temperature of said solution is kept and the said reaction continuously takes place for 3 h. TLC is conducted to check the completeness of said reaction. Dichloromethane is added to extract the water phase, and the organic phase is considered as waste solution, wherein the said dichloromethane is recovered from said organic phase. 31% HCl is added to said extracted water phase until the resulting pH value is 1~2, and then it is cooled to 10° C. and kept at said temperature for 0.5 h, the obtained is vacuum filtered and dried, in this way, 95 g final product is obtained, and the resulting yield is 95%.

Figure 5:
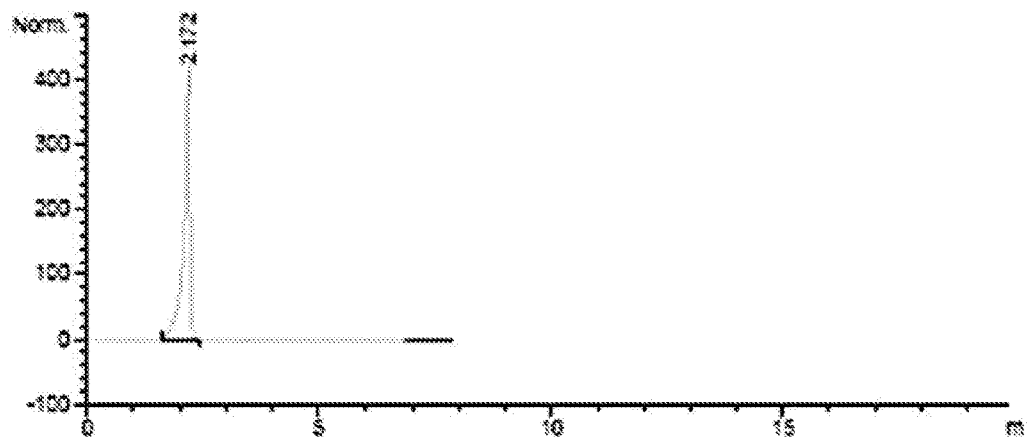
FIG. 5 is HPLC spectrum of 3-(difluoromethyl)-1-methyl-1H-pyrazol-4-carboxylic acid synthesized in Example 1 of the present invention.

As shown in FIG. 5, the said final product is analyzed with HPLC to verify its purity, and the obtained results are listed in Table 3.

TABLE 3

HPLC results obtained from 3-(difluoromethyl)-1-methyl-1H-pyrazol-4-carboxylic acid

| Peak no. | Retention time (min) | Peak height | Peak area | Content (%) |
|---|---|---|---|---|
| 1 | 2.172 | 417.05890 | 3670.01538 | 100.0000 |
| Total | 2.172 | 417.05890 | 3670.01538 | 100.0000 |

Figure 6:
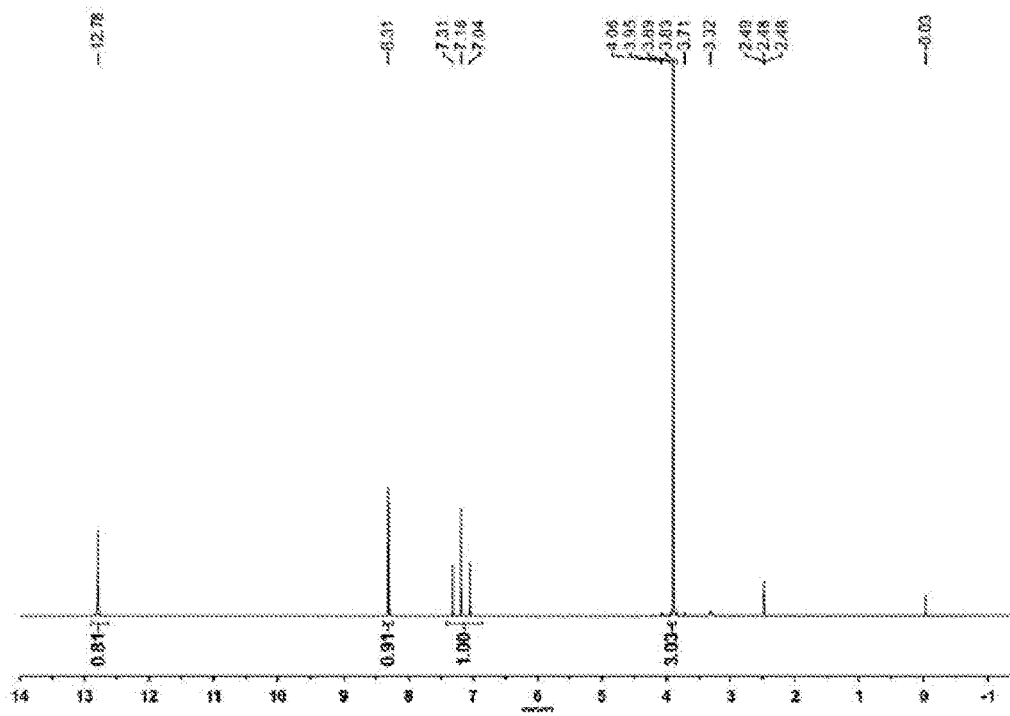
FIG. 6 is NMR spectrum of 3-(difluoromethyl)-1-mehtyl-1H-pyrazol-4-carboxylic acid synthesized in Example 1 of the present invention.

As shown in FIG. 6, HPLC is used to check the purity of said final product, and then HNMR is conducted with the aid of Bruker 400M NMR spectrometer, wherein DMSO-D6 is chosen as solvent, and the obtained HNMR results are shown as follows:

HNMR (DMSO-D6, 400M): δ=12.78 (s, 1H), 8.31 (s, 1H), 7.18 (t, J1=56 Hz, J2=52 Hz, 1H), 3.89 (s, 1H).

And therefore, the composition of said final product is determined as 3-(difluoromethyl)-1-methyl-1H-pyrazol-4-carboxylic acid.

Example 2

Method for the preparation of 3-(difluoromethyl)-1-methyl-1H-pyrazol-4-carboxylic acid, wherein it comprises the following steps:

Preparation of 3-dimethylamino methylene-1,1-difluoro-2,4-pentanedione 565 mL dichloromethane solution containing dimetylamino vinyl methyl ketone is added to a three-neck flask, the said solution contains 113 g (1.0 mol) dimethylamino vinyl methyl ketone. The said solution is cooled to −5° C. in the presence of nitrogen. Subsequently, 119 g (1.2 mol) difluoroacetyl fluorine gas is introduced. The temperature of said system is controlled to below 0 C during addition of said gas, at the end of addition; the said mixture is mixed for 2 h at said temperature. The obtained reaction solution is vacuum condensed to remove the said solvent with the aid of rotary evaporator, the obtained is crude 3-dimethylaminomethylene-1,1-difluoro-2,4-pentanedione, the resulting gas-phase purity is above 95%, the said crude product is directly used in the following reaction based on quantitative yield.

Preparation of 3-difluoromethyl-1-methyl-4-acetyl pyrazol

40% methylydrazine water solution is added to a three-neck flask, wherein the said solution contains 126 g (1.1 mol). The said solution is cooled to −20° C., subsequently, the said dichloromethane solution containing 3-dimethylamino methylene-1,1-difluoro-2,4-pentanedione is added to said flask, the said addition takes place at −25~−20° C., at the end of said addition, the said mixture is kept at said temperature for 1 h. Once GC shows raw materials are completely reacted, the said mixture is heated to room temperature, subsequently, water phase is separated, the obtained organic phase is condensed, and then it is recrystallized and dried, in this way, 150 g white solid is obtained, and the resulting yield is 86%.

Preparation of 3-(difluoromethyl)-1-methyl-1H-pyrazol-4-carboxylic acid 887.5 g 10% NaClO water solution is added to a three-neck flask. The said reaction solution is cooled to 10° C. Subsequently, 100 g 3-difluoromethyl-1-methyl-4-acetyl pyrazol is dissolved in 100 mL methanol, leading to formation of organic solution. The said organic solution is slowly added to the said flask. The temperature of said addition is kept at 10~15° C. At the end of said addition, the temperature of said solution is kept and the said reaction continuously takes place for 3 h. TLC is conducted to check the completeness of said reaction. Dichloromethane is added to extract the water phase, and the organic phase is considered as waste solution, wherein the said dichloromethane is recovered from said organic phase. 31% HCl is added to said extracted water phase until the resulting pH value is 1~2, and then it is cooled to 10 C and kept at said temperature for 0.5 h, the obtained is vacuum filtered and dried, in this way, 95 g final product is obtained, and the resulting yield is 95%.

Example 3

Method for the preparation of 3-(difluoromethyl)-1-methyl-1H-pyrazol-4-carboxylic acid, wherein it comprises the following steps:

Preparation of 3-dimethylamino methylene-1,1-difluoro-2,4-pentanedione 565 mL dichloromethane solution containing dimetylamino vinyl methyl ketone is added to a three-neck flask, the said solution contains 113 g (1.0 mol) dimethylamino vinyl methyl ketone. The said solution is cooled to −5° C. in the presence of nitrogen. Subsequently, 108 g (1.1 mol) difluoroacetyl fluorine gas is introduced. The temperature of said system is controlled to below 0° C. during addition of said gas, at the end of addition; the said mixture is mixed for 2 h at said temperature. The obtained reaction solution is vacuum condensed to remove the said solvent with the aid of rotary evaporator, the obtained is crude 3-dimethylaminomethylene-1,1-difluoro-2,4-pentanedione, the resulting gas-phase purity is above 95%, and the said crude product is directly used in the following reaction based on quantitative yield.

Preparation of 3-difluoromethyl-1-methyl-4-acetyl pyrazol

40% methylhydrazine water solution is added to a three-neck flask, wherein the said solution contains 137 g (1.2 mol). The said solution is cooled to −20° C., subsequently, the said dichloromethane solution containing 3-dimethylamino methylene-1,1-difluoro-2,4-pentanedione is added to said flask, the said addition takes place at −25~−20° C., at the end of said addition, the said mixture is kept at said temperature for 1 h. Once GC shows raw materials are completely reacted, the said mixture is heated to room temperature, subsequently, water phase is separated, the obtained organic phase is condensed, and then it is recrystallized and dried, in this way, 147 g white solid is obtained, and the resulting yield is 85%.

Preparation of 3-(difluoromethyl)-1-methyl-1H-pyrazol-4-carboxylic acid 500 g 20% NaOH water solution is added to a three-neck flask, 160 g bromine is added in the presence of ice bath, at the end of said addition, the said mixture is kept at a temperature below 10° C., subsequently, 87 g 3-difluoromethyl-1-methyl-4-acetyl pyrazol is dissolved in 90 mL methanol, leading to formation of organic solution. The said organic solution is slowly added to the said flask. The temperature of said addition is kept at 10~15 C. At the end of said addition, the temperature of said solution is kept and the said reaction continuously takes place for 3 h. TLC is conducted to check the completeness of said reaction. Dichloromethane is added to extract the water phase, and the organic phase is considered as waste solution, wherein the said dichloromethane is recovered from said organic phase. 31% HCl is added to said extracted water phase until the resulting pH value is 1~2, and then it is cooled to 10° C. and kept at said temperature for 0.5 h, the obtained is vacuum filtered and dried, in this way, 84 g final product is obtained, and the resulting yield is 96%.

Example 4

Method for the preparation of 3-(trifluoromethyl)-1-methyl-1H-pyrazol-4-carboxylic acid (CAS no.: 113100-53-1), wherein it comprises the following steps:

Preparation of 3-dimethylamino methylene-1,1,1-trifluoro-2,4-pentanedione 250 mL dichloromethane solution containing dimetylamino vinyl methyl ketone is added to a three-neck flask, the said solution contains 57 g (0.5 mol) dimethylamino vinyl methyl ketone. The said solution is cooled to −5° C. in the presence of nitrogen. Subsequently, 73 g (0.55 mol) trifluoroacetyl fluorine gas is introduced. The temperature of said system is controlled to below 0 C during addition of said gas, at the end of addition; the said mixture is mixed for 2 h at said temperature. The obtained reaction solution is vacuum condensed to remove the said solvent with the aid of rotary evaporator, the obtained is crude 3-dimethylaminomethylene-1,1,1-trifluoro-2,4-pentanedione, the resulting gas-phase purity is above 95%, the said crude product is directly used in the following reaction based on quantitative yield.

Preparation of 3-trifluoromethyl-1-methyl-4-acetyl pyrazol

40% methylhydrazine water solution is added to a three-neck flask, wherein the said solution contains 63 g (0.55 mol). The said solution is cooled to −20° C., subsequently, the said 3-dichloromethane solution containing 3-dimethylamino methylene-1,1,1-trifluoro-2,4-pentanedione is added to said flask, the said addition takes place at −25~−20° C., at the end of said addition, the said mixture is kept at said temperature for 1 h. Once GC shows raw materials are completely reacted, the said mixture is heated to room temperature, subsequently, water phase is separated, the obtained organic phase is condensed, and then it is recrystallized and dried, in this way, 86.4 g 3-trifluoromethyl-1-methyl-4-acetyl pyrazol is obtained, and the resulting yield is 90%.

Preparation of 3-(trifluoromethyl)-1-methyl-1H-pyrazol-4-carboxylic acid 500 g 20% NaOH water solution is added to a three-neck flask, 160 g bromine is added in the presence of ice bath, at the end of said addition, the said mixture is kept at a temperature below 10 C, subsequently, 96 g 3-trifluoromethyl-1-methyl-4-acetyl pyrazol is dissolved in 100 mL methanol, leading to formation of organic solution. The said organic solution is slowly added to the said flask. The temperature of said addition is kept at 10~15 C. At the end of said addition, the temperature of said solution is kept and the said reaction continuously takes place for 3 h. TLC is conducted to check the completeness of said reaction. Dichloromethane is added to extract the water phase, and the organic phase is considered as waste solution, wherein the said dichloromethane is recovered from said organic phase. 31% HCl is added to said extracted water phase until the resulting pH value is 1~2, and then it is cooled to 10° C. and kept at said temperature for 0.5 h, the obtained is vacuum filtered and dried, in this way, 92 g final product is obtained, and the resulting yield is 95%.

Example 5

Method for the preparation of 3-(difluoromethyl)-1-methyl-1H-pyrazol-4-carboxylic acid, wherein it comprises the following steps:

Preparation of 3-dimethylamino methylene-1-chloro-1,1-difluoro-2,4-pentanedione 560 mL dichloromethane solution containing dimetylamino vinyl methyl ketone is added to a three-neck flask, the said solution contains 113 g (1.0 mol) dimethylamino vinyl methyl ketone. The said solution is cooled to −5° C. in the presence of nitrogen. Subsequently, 164 g (1.1 mol) difluoroacetyl chlorine gas is introduced. The temperature of said system is controlled to below 0 C during addition of said gas, at the end of addition; the said mixture is mixed for 2 h at said temperature. The obtained reaction solution is vacuum condensed to remove the said solvent with the aid of rotary evaporator, the obtained is crude 3-dimethylaminomethylene-1,1,1-trifluoro-2,4-pentanedione, the resulting gas-phase purity is above 95%, the said crude product is directly used in the following reaction based on quantitative yield.

Preparation of 3-difluoromethyl-1-methyl-4-acetyl pyrazol

40% methylydrazine water solution is added to a three-neck flask, wherein the said solution contains 126 g (1.1 mol). The said solution is cooled to −20° C., subsequently, the said dichloromethane solution containing 3-dimethylamino methylene-1-chloro-1,1-difluoro-2,4-pentanedione is added to said flask, the said addition takes place at −25~−20° C., at the end of said addition, the said mixture is kept at said temperature for 1 h. Once GC shows raw materials are completely reacted, the said mixture is heated to room temperature, subsequently, water phase is separated, the obtained organic phase is condensed, and then it is recrystallized and dried, in this way, 184 g 3-difluorochloromethyl-1-methyl-4-acetyl pyrazol is obtained, and the resulting yield is 88%.

Preparation of 3-(difluorochloromethyl)-1-methyl-1H-pyrazol-4-carboxylic acid 887.5 g 10% NaClO water solution is added to a three-neck flask. The said reaction solution is cooled to 10° C. Subsequently, 105 g 3-difluorochloromethyl-1-methyl-4-acetyl pyrazol is dissolved in 100 mL methanol, leading to formation of organic solution. The said organic solution is slowly added to the said flask. The temperature of said addition is kept at 10~15° C. At the end of said addition, the temperature of said solution is kept and the said reaction continuously takes place for 3 h. TLC is conducted to check the completeness of said reaction. Dichloromethane is added to extract the water phase, and the organic phase is considered as waste solution, wherein the said dichloromethane is recovered from said organic phase. 31% HCl is added to said extracted water phase until the resulting pH value is 1~2, and then it is cooled to 10° C. and kept at said temperature for 0.5 h, the obtained is vacuum filtered and dried, in this way, 100 g 3-(difluorochloromethyl)-1-methyl-1H pyrazol-4-carboxylic acid is obtained, and the resulting yield is 95%.

Examples 6 and 7 describe the transformation of a 3-fluoroalkyl-1-methylpyrazol-4-carboxylic acid via its carboxylic acid halide into a pesticide, which preferably is an amide fungicide, as described in the textbooks "Bioactive Heterocyclic Compound Classes", Editors C. Lamberth and J. Dinges, Wiley 2012, p. 175-193 (Chapter 15, Pyrazole Carboxamide Fungicides Inhibiting Succinate Dehydrogenase) and "Modern Crop Protection Compounds", eds. W. Krämer, U. Schirmer, P. Jeschke, and M. Witschel, Wiley 2012, p. 627-639 and the references cited in these textbooks.

Example 6

3-(difluoromethyl)-1-methyl-1H-pyrazol-4-carboxylic acid obtained by example 2 is treated with oxalyl chloride (1.25 eq) in toluene, and a few drops of dimethylformamide are added. The mixture is concentrated under reduced pressure to yield the carboxyl chloride.

Example 7

(1.3 mmol) 3',4'-dichloro-5-fluoro-1,1'-biphenyl-2-amine and (1.56 mmol) 3-(difluorochloromethyl)-1-methyl-1H-pyrazol-4-carboxylic acid chloride obtained by Example 6 are solved in 6 ml tetrahydrofuran and mixed with 2.6 mmol triethylamin. The mixture is stirred for 16 h at 60° C. The mixture is concentrated and chromatographed on silica using cyclohexane/acetic acid ethyl ester to yield bixafen. It shall be noted that the said Examples are only used for illustrative purposes; the present invention shall not be limited by said Examples. Changes or modifications of present invention might be made by those skilled in the art. It is unnecessary and impossible to illustrate all Examples of the present invention. However, obvious changes or modifications based on the spirit of the present invention are still within the scope of the present invention.

The invention claimed is:
1. A method for the preparation of a pesticide, the method comprising preparing a 3-fluoroalkyl-1-methylpyrazol-4-carboxylic acid by the following steps:

step 1, fluoroacetyl fluoride derivative shown in Formula I undergoes condensation with dimethyl amino vinyl methyl ketone, as a result, 3-dimethylamino methylene-1,1-difluoro-2,4-pentanedione derivative shown in Formula II is formed:

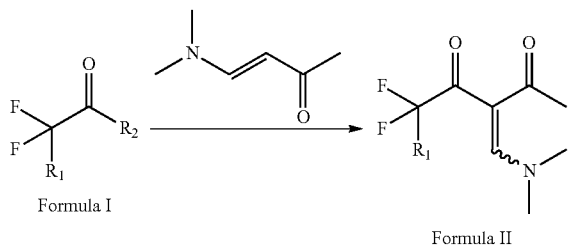

Formula I    Formula II wherein, $R_1$ is hydrogen, fluorine or chlorine atom; $R_2$ is fluorine or chlorine atom;

step 2, ring closing reaction takes place between said 3-dimethylamino methylene-1,1-difluoro-2,4-pentanedione shown in Formula II and methylhydrazine, in this way, 3-fluoroalkyl-1-methyl-4-acetyl pyrazol derivative shown in Formula III is obtained;

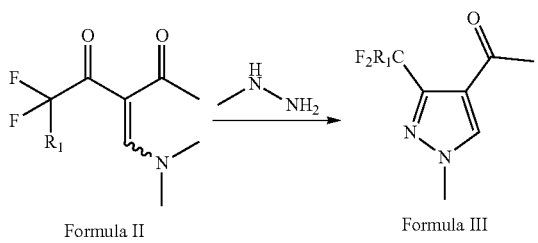

Formula II    Formula III step 3, the said 3-fluoroalkyl-1-methyl-4-acetyl pyrazol derivative shown in Formula III is oxidized in the presence of alkali, and then acidified, in this way, 3-fluoroalkyl-1-methylpyrazol-4-carboxylic acid shown in Formula IV is formed,

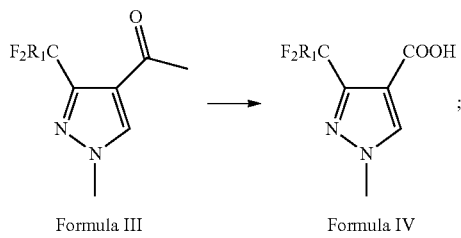

Formula III    Formula IV and transforming the 3-fluoroalkyl-1-methylpyrazol-4-carboxylic acid into an activated 3-fluoroalkyl-1-methylpyrazol-4-carboxylic acid and reacting the activated 3-fluoroalkyl-1-methylpyrazol-4-carboxylic acid with an amine to obtain the pesticide.

2. The method according to claim 1, wherein in step 1, a gas of the said fluoro acetyl derivative of Formula I is directly introduced to a dichloromethane solution containing dimethyl amino vinyl methyl ketone, and the reaction temperature is −5~0° C.

3. The method according to claim 1, wherein in step 2, the reaction temperature is −40~0° C., the reaction time is 1~8 h, and the molar ratio between said methylhydrazine and 3-dimethylamino methylene-fluoro-2,4-pentanedione of Formula II is 1.1:1~1.5:1.

4. The method of claim 3, wherein the said reaction temperature of said step 2 is −25~20° C., and the reaction time is 1~2 h.

5. The method according to claim 1, wherein in step 3, sodium hypochlorite solution or sodium hypobromite solution is used in the oxidation in the presence of alkali, the said sodium hypochlorite solution is prepared by introducing chlorine gas to sodium hydroxide water solution, and the said sodium hypobromite solution is prepared by introducing liquid bromine to sodium hydroxide water solution.

6. The method according to claim 1, wherein in step 3, the reaction temperature is 0~50° C., and the reaction time is 1~5 h.

7. The method of claim 6, wherein in step 3, the reaction temperature is 10~20° C., and the reaction time is 2~3 h.

8. The method of claim 6, wherein HCl solution is used in said acidification, and the final pH value of said solution is adjusted to 1~2.

9. The method according to claim 1, wherein said fluoroacetyl fluoride derivative of Formula I is difluoroacetyl fluorine, said 3-fluoroalkyl-1-methylpyrazol-4-carboxylic acid of Formula IV is 3-(difluoromethyl)-1-methyl-1H-pyrazol-4-carboxylic acid.

10. The method according to claim 1, wherein the pesticide is a fungicide amide.

11. The method according to claim 10, wherein the pesticide is Bixafen, Fluxapyroxad, Isopyrazam or Sedaxane.

12. The method according to claim 1, wherein the activated 3-fluoroalkyl-1-methylpyrazol-4-carboxylic acid is a carboxylic acid halide.

13. The method according to claim 1, wherein the amine is aniline.

* * * * *